United States Patent
Lodaya et al.

(10) Patent No.: US 6,420,581 B1
(45) Date of Patent: Jul. 16, 2002

(54) MANUFACTURE OF ZINC HEXASULFIDE AMINE COMPLEXES

(75) Inventors: Jayant S. Lodaya, Akron; Otto W. Maender, Copley; Paul M. Mitchem, Akron, all of OH (US)

(73) Assignee: Flexsys America L.P., Akron, OH (US)

( * ) Notice: Subject to any disclaimer, the term of this patent is extended or adjusted under 35 U.S.C. 154(b) by 0 days.

(21) Appl. No.: 09/605,777

(22) Filed: Jun. 28, 2000

Related U.S. Application Data

(60) Provisional application No. 60/141,418, filed on Jun. 29, 1999.

(51) Int. Cl.$^7$ .................................................. C07F 3/06
(52) U.S. Cl. ........................... 556/130; 548/101; 546/2; 544/64; 544/225
(58) Field of Search .................. 556/130; 548/101; 546/2; 544/64, 225

(56) References Cited

U.S. PATENT DOCUMENTS

| | | | |
|---|---|---|---|
| 5,171,847 A | 12/1992 | Snaith et al. | .................. 534/16 |
| 5,206,394 A | 4/1993 | Snaith et al. | ................ 549/429 |
| 6,114,469 A | 9/2000 | Rauchfuss et al. | .......... 525/343 |

FOREIGN PATENT DOCUMENTS

| | | | | |
|---|---|---|---|---|
| EP | 0 407 121 | 1/1991 | ............. | C07F/3/00 |
| EP | 0 317 087 | 9/1992 | ............. | C07F/1/00 |
| GB | 1 236 055 | 6/1971 | ............. | C08D/7/02 |
| GB | 2 231 569 | 11/1990 | ......... | C07C/211/09 |
| GB | 2 254 610 | 10/1992 | ............. | C07F/1/00 |

OTHER PUBLICATIONS

Abstract No. 91–010079/02, EP 407–121–A, Jan. 9, 1991.
Abstract No. 90–350816/47, GB 2231–569–A, Nov. 21, 1990.
Abstract No. 92–342416/42, GB 2254610–A, Oct. 14, 1992.
Abstract No. 92–000252/01, DD 292463–A, Aug. 1, 1991.
Abstract No. 127 12501t, A study of synthesis and characteristics of zinc complex with $S_a$ 2and 2–methylpridine ligands.
Abstract No. 1990:209817, Journal American Chemical Society (1990), 112(10), 4043–4.
Effect of Ancillary Ligands on the Reacitivey and Structure of Zinc Polysulfido Complexes, Robert J. Pafford and Thomas B. Rauchfuss, Inorganic Chemical 1998, 37 1974–1980m w/Abstract No. 1998–229698 attached.
Abstract No. 89–150744/20, WO 8903–835–A, May 5, 1989.
Donor Solvent Mediate Reactions of Elemental Zinc and Sulfur, sans Explosion, Atul K. Verma, Thomas B. Rauchfuss and Scot R. Wilson, Inorganic Chemistry, 1995, 34.
Direct Approaches to Zinc Polychalcogenide Chemistry: $ZnS_6(N-Melm)_2$ and $Znse_4(N-Melm)_2$, Journal of the American Chemical Society 1990, 112.
Studies in Inorganic Chemistry 5, Sulfur, Its Significance for Chemistry, for the Geo–, Bio–and Cosmosphere and Technology, pp. 311–329.
Search Report, Jan. 12, 1999.

*Primary Examiner*—Porfirio Nazario-Gonzalez
(74) *Attorney, Agent, or Firm*—Louis A. Morris

(57) ABSTRACT

A process for the manufacture of zinc hexasulfide amine complexes comprising reacting zinc, sulfur and a molar excess of amine at an elevated temperature to obtain a reaction mixture comprising zinc hexasulfide amine complexes and excess amine. A first solvent in which the zinc hexasulfide amine complexes are largely not soluble is added to obtain a slurry of the reaction mixture. The zinc hexasulfide amine complexes may be recovered in a subsequent separation process.

8 Claims, No Drawings

MANUFACTURE OF ZINC HEXASULFIDE AMINE COMPLEXES

The present application claims priority of U.S. Provisional Patent Application Serial No. 60/141,418, filed Jun. 29, 1999, the content of which is incorporated by reference herein in its entirety.

BACKGROUND OF THE INVENTION

1. Field of the Invention

This invention involves the preparation of zinc hexasulfide amine complexes.

2. Prior Art

Complexes of zinc hexasulfide with an amine are described in an article in the publication, "Direct Approaches to Zinc Polychalcogenide Chemistry: $ZnS_6$(N-MeIm)$_2$ and $ZnSe_4$(N-MeIm)$_2$" by Dev, Ramli, Rauchfuss and Stern, JACS 112, 6385 (1990). The article describes the preparation and properties of the complexes, and suggests that they are "relevant to the action of zinc catalysts for the addition of polysulfur radicals to polyolefins in the rubber vulcanization process."

It is known to make zinc hexasulfide amine complexes (as shown in JACS 112, 6385) by reacting zinc powder, sulfur and a molar excess of the appropriate amine at an elevated temperature; then cooling the reaction product to room temperature and diluting with ethanol. The product appears, on cooling, as a yellow powder which is recovered by filtration. While the zinc hexasulfide amine complexes can be made by this general process, it is also known to produce one complex from another by amine substitution, whereby the desired amine is reacted with a completed complex, displacing the amine from the complex and substituting the desired amine thereon.

In the article "Donor Solvent Mediated Reactions of Elemental Zinc and Sulfur, sans Explosion", Verma et al, Inorganic Chemistry, 1995, pages 3072–3078, there is a teaching of a reaction of zinc dust, sulfur and N-methylimidazole (MeIm) at 90° C. for a few hours. The reaction mixture is diluted with a nonpolar solvent which leads to precipitation of yellow microcrystals of $ZnS_6$-(MeIm)$_2$. In the experimental section of the article it is mentioned that the zinc used was –325 mesh, which would be less than 45 microns.

It has been found that zinc hexasulfide amine complexes, as made by the process of the present invention and included in effective amounts in vulcanizable rubber, give compositions which vulcanize much faster, more quickly than the formulations previously in use. Specifically, the presence of zinc hexasulfide amine complexes in an amount of from 0.1 to 10 parts by weight per 100 parts by weight of vulcanizable rubber, proves to be effective in producing vulcanizates with fast cure rates and superior physical properties.

SUMMARY OF THE INVENTION

In one embodiment the present invention is a process for the manufacture of zinc hexasulfide amine complexes comprising reacting zinc, sulfur and a molar excess of amine at an elevated temperature to obtain a reaction mixture comprising zinc hexasulfide amine complexes and excess amine. Most of the excess amine may be separated from solid zinc hexasulfide amine complexes in the reaction mixture by techniques such as decantation, filtering and/or siphoning. A first solvent is added to the reactants or to the reaction mixture in which the zinc hexasulfide amine complexes are largely not soluble in an amount sufficient to obtain a slurry of the reaction mixture in the first solvent suitable for a subsequent separation process in which zinc hexasulfide amine complexes are to be recovered. The zinc hexasulfide amine complexes product is recovered as a solid in the subsequent separation process.

In a second embodiment the present invention is a process for the manufacture of zinc hexasulfide amine complexes comprising reacting zinc, which is at least about 99.5% pure with a particle size –100 mesh, with sulfur and a molar excess of amine at an elevated temperature. A reaction mixture is obtained comprising zinc hexasulfide amine complexes and excess amine. Most of the excess amine may be separated from solid zinc hexasulfide amine complexes in the reaction mixture by techniques such as decantation, filtering and/or siphoning. A solvent is added to the remaining reaction mixture in which the zinc hexasulfide amine complexes are not soluble. The zinc hexasulfide amine complexes product is recovered by filtering zinc hexasulfide amine complexes as solids from the reaction mixture and drying the solids to obtain the product.

Other embodiments of the present invention are based on details including reaction conditions, reactant and solvent compositions and process details, all of which are hereinafter disclosed in the following discussion of each of these facets of the invention.

DETAILED DESCRIPTION OF THE INVENTION

The reaction of the process of the invention is most effectively conducted at a temperature of from about 50° C. to about 125° C. for about 0.5 hours to about 10 hours.

Complexes of zinc hexasulfide and an amine that are effective in the compositions of the invention include zinc hexasulfide which has been complexed with an amine of from 3 to 24 carbon atoms. Preferred amines include tertiary amines and tertiary diamines, or mixtures thereof. Among these preferred amines are N,N,N',N'-tetramethylethylenediamine (TMEDA), 1,1,3,3-tetramethylguanidine, 1-Butylimidazole, 1,2-Dipiperidinoethane, 1,2-Dimorpholinoethane, 1,2-Di-(N-Methylpiperazino) ethane, N-Methylimidazole, 1-Benzyl-2-methylimidazole, 1,2-Dimethylimidazole, N-3-Aminopropylimidazole, 1-Vinylimidazole, 1-Allylimidazole, N-Cyclohexyl-N',N',N'',N''-tetramethylguanidine and 4-Dimethylaminopyridine, or mixtures thereof.

The preferred amine is N,N,N',N'-tetramethylethylenediamine, and particularly preferred to be at least about 85% N,N,N',N'-tetramethylethylenediamine and less than about 2 wt. % water.

There should be a sufficient amount of first solvent added to the reactants or reaction mixture to reduce the amount of amine required in the process to be a little or moderately in excess of the stoichiometric requirement for an effective reaction as opposed to a large excess. A preferred amount of added first solvent will reduce the amount of amine required from about 2 to about 6 times the stochiometric amount.

It would be advantageous for most of the excess amine to be separated as a supernatant from solid zinc hexasulfide amine complexes in the reaction mixture prior to addition of the first solvent by a technique such as decantation, filtering and/or siphoning. When most of the excess amine is separated from solid zinc hexasulfide amine complexes in the reaction mixture the product may be washed with the first solvent to remove excess amine and impurities.

The zinc hexasulfide amine complexes may be separated from the reaction mixture as a cake of solids, and the cake washed to minimize color and/or odor from zinc hexasulfide amine complexes product. The cake may be washed with an aqueous solution of a caustic or hypochlorite.

The amine may not be miscible with the first solvent. In that case, the reaction mixture may be filtered and the product washed with the first solvent. The filtrate would form two liquid phases comprising a first solvent phase and an amine phase, the first solvent and amine being recycled and reused in the process.

The first solvent may comprise saturated hydrocarbons, aromatic hydrocarbons or alcohols, preferably included in the group of hexanes, heptanes, toluenes, xylenes, methanol, ethanol and propanol.

The solid zinc hexasulfide amine complexes may be purified by being dissolved in a second solvent in which they are soluble, followed by separating the resulting solution from insolubles and precipitating the complexes by adding first solvent to the solution. The second solvent could comprise chloroform, methylene chloride or N-methyl-2-pyrrolidone (NMP).

It was surprisingly discovered that when at least about 99.5% pure zinc was used in the reaction of the invention, preferably with a particle size of −100 mesh (all particles that are less than 150 microns will fall through a 100 mesh screen), the amount of amine (TMEDA) that can be removed by decantation, filtering and/or siphoning following the reaction is significantly more than with a less pure zinc of a particle size of less than 10 microns. Even more surprising was the finding that the product had properties similar to the recrystallized product produced in the laboratory. These findings are very important, since ease of removal of excess amine would cut down the requirements of distilling amine from the amine/first solvent filtrate recovered from the product separation process in view of there being less amine in that filtrate, and a product close to the quality of recrystallized product can be obtained which results in improved performance of the crude product in rubber. Furthermore, the need to introduce exotic solvents such as NMP, chloroform and methylene chloride, which are solvents of choice for recrystallization of this product, is eliminated.

The above article from *Inorganic Chemistry* teaches the importance of grain size of the zinc (−325 mesh is the size mentioned), the smaller the grain size the better the reaction. One would therefore be led to believe by this article that it would be pointless to go to a much larger particle size, such as 100 microns or greater, because doing so would limit the reaction. One of ordinary skill in the art would thus be dissuaded by this reference from employing larger particle size zinc that would result in larger particle size product and would facilitate separation of product from the reaction mixture, because he would believe the reaction could not be made to occur.

This finding enables the use of large particle size high purity zinc, i.e. at least about 99.5% pure, to obtain a product having quality significantly better than what is obtained from less pure zinc with less than 10 micron particle size, the usual commercial grade. The performance of the product derived from 99.5% or better zinc in rubber is as good as that from recrystallized product. Thus the use of 99.5% or purer zinc is a particularly preferred embodiment of the invention.

Even more fundamental, however, is that *Inorganic Chemistry* teaches dilution of the cooled reaction mixture with a nonpolar solvent to recover product by precipitation. In the present invention there is no need to add any additional solvent to precipitate product, since the product is largely insoluble in the excess amine present and decantation of excess amine may be performed without addition of another solvent. The product is also largely insoluble (less than 5 wt. %) in the first solvent that is added to the reactants or reaction mixture in accordance with the present invention to obtain a slurry from which the product may be removed by simple filtration.

Whatever little solubility the product may have in the amine does not necessarily negatively impact the process, because the decanted amine may be recycled. The recycled amine would be saturated with product so there would be no significant loss in the unreacted/excess amine. The result is increased yield of product.

With regard to a general procedure for carrying out the present invention, the following non-limiting discussion is intended to provide illustrations of preferred embodiments. In a typical experiment, a reactor equipped with heating mantle, mechanical stirrer, thermocouple, condenser and a nitrogen purge line is charged with zinc, sulfur and amine (N,N,N',N'-tetramethylethylenediamine-TMEDA). The best charging system has been found to be: first charging part of the amine and adding all of the sulfur while stirring. This mixture is stirred for a few minutes to make thick slurry and then zinc is added slowly while stirring so that it does not settle to the bottom of the reactor and remains dispersed throughout the reaction mixture. Finally, the rest of the amine is added to clean up the residual material in the addition funnel thereby effectively bringing all of the raw materials to the reactor.

The mixture is then heated to typically about 90° C. for about 2 hours. During this time the reaction goes through an exotherm and the temperature could go up as high as 125° C. The reaction mixture color goes through different shades of green. After a reaction time of about 2 hr at 90° C., the reaction mixture is typically cooled to about 70° C. and excess amine is decanted off using a fritted glass tube and by applying vacuum to remove liquid while leaving behind solids in the reactor. There could be some loss of material due to the solubility of product in amine, which would be more at higher temperature. Hence, cooling further down to a lower temperature and then performing decantation could potentially give higher yields due to less loss of material. Other techniques could be used to separate liquid from solids. One can filter the solids at this point and wash the solids with an appropriate solvent (typically methanol). The filtrate and washings could be kept separate and the filtrate can be recycled back. Washings containing amine and solvent can be separated by distillation or phase separation and recycled, or could be reused without further separation.

To the remaining mass in the reactor, an appropriate solvent (typically methanol) is added and the mixture is stirred before filtering the mixture to give product. The product is then washed with solvent and then dried. The product is a greenish yellow solid with melting point greater than 145–150° C., typically 155–160° C. The product is isolated in yields as high as 96%.

Instead of isolating the product and then recrystallizing, in the above mentioned process, after decantation of amine, one can perform recrystallization. A solvent such as N-methyl-2-pyrrolidone (NMP) or chloroform etc in which product is soluble can be added, insolubles removed via filtration or centrifugation, and then a solvent in which product is insoluble such as methanol, hexanes, heptanes etc can be added to the filtrate to crystallize/precipitate the solids.

Various process parameters have been studied.

1. Mixing rate (stirrer type and speed): Proper mixing of reactants is desired to get optimum yields of product. If mixing is not good then zinc, being heavy, will settle to the bottom of the reactor and may form a large lump that would not be reactive and in turn would give lower yields. The effect of stirring speed (RPM) on yield is evident, i.e. higher stirring will give better yields by effectively utilizing all of the zinc. Another plausible explanation is that at higher speeds zinc would not fall to the bottom, but would remain suspended in the reaction mixture.

2. Sulfur: Rubber makers sulfur may be used. Other grades of sulfur have also been successfully evaluated. The preferred sulfur level is 6 moles for every mole of zinc, however, a small excess of sulfur (2–6% in excess of the molar requirement) will give better results.

3. Zinc: In most experiments 98+% pure zinc (but less than 99.5%) from Aldrich with less than 10 micron particle size was used. In other experiments 99.9% zinc with −100 mesh (less than 150 micron) particle size from Johnson Matthey was used. It was surprising to see a significantly higher amount of TMEDA being decanted from the experiments when 99.9% zinc (−100 mesh) was used compared to 98+% grade from Aldrich. Furthermore, quality of product from this 99.9% assay zinc was significantly better than the one with 98+% zinc. This was very evident when these products were mixed in rubber and evaluated for various properties from the performance point of view. The performance of the product derived from 99.9% zinc experiment was as good as that from recrystallized product. The recrystallization step is tedious and results in significant yield loss and is economically and environmentally undesirable. Use of 99.9% pure zinc offers an option of obtaining a product which is as good as recrystallized product yet does not experience yield loss nor significantly higher cost. Also, it avoids introduction of exotic solvents such as NMP, chloroform and methylene chloride which are solvents of choice for recrystallization of this product.

Furthermore, 99.9% zinc with −100 mesh particle size gives a significantly higher amount of TMEDA upon decantation. The greater the amount of TMEDA during decantation, the less TMEDA that will end up with solvent and hence the lower amount of TMEDA that need be recovered by distillation. This itself offers significant cost savings from the standpoint of manufacturing cost.

4. N,N,N',N'-Tetramethylethylenediamine (TMEDA): Different grades of TMEDA from different suppliers have been successfully evaluated. Several recycle studies were carried out successfully using decanted TMEDA. It was found that batches using decanted/recycled TMEDA gave significantly higher yields compared to when just fresh TMEDA was used. This could be due to the fact that the decanted TMEDA is saturated with product and when it is reused, there is no additional loss of product due to solubility in TMEDA.

5. Reaction time and temperature: Two hours at 90° C. seems sufficient to complete the reaction. During this time the reaction goes through an exotherm and the temperature may go up as high as 123° C. If the exotherm is controlled by effective cooling, the reaction could take longer. It was also demonstrated that lower reaction temperatures (70 to 80° C.) can be used, however, the reaction time increases. There is no adverse effect on product quality due to lower temperature and the exotherm can be controlled better.

6. Effect of solvent: Most experiments have been carried out using excess TMEDA. In most cases the amount of TMEDA used was about 6.6 moles for every mole of zinc. When the stoichiometric amount of TMEDA was used (1 mole for every mole of zinc) along with solvent such as heptane or decane, desired product was not obtained even after reaction for several hours.

However part of the TMEDA may be replaced with methanol and product still be successfully made. In one experiment 85% by weight of normally used 6.6 moles of TMEDA per mole of zinc was employed and the rest of the weight was compensated for with methanol. For example, 40.8 g zinc, 120.2 g sulfur, 408 g TMEDA and 72 g methanol (if methanol was not used then 481 g of TMEDA would have been employed) were mixed and heated for 6 hours at 86° C. The reaction temperature stabilized at 86° C. and the mixture was refluxed for 6 hours, although far less than 6 hours may have been sufficient. One advantage associated with this system was that the temperature was easy to control since it would not exceed reflux temperature due to the presence of solvent. Furthermore, the most expensive raw material, namely TMEDA, was used in a smaller excess than ordinarily required.

In a similar experiment, 50% by weight of the usual 6.6 moles TMEDA per mole of zinc (resulting in use of 3.3 times the stoichiometric amount of amine) was replaced with methanol and the reaction carried out for 7 hours at 72° C. The reaction temperature stabilized at 72° C. while under reflux. For example, 20.0 g zinc, 60.7 g sulfur, 117.5 g TMEDA (as opposed to 235 g if solvent was not used) and 117.5 g methanol were mixed and heated for 7 hours at 72° C. The product was obtained in 91.3% yield. Once again, similar advantages to those described above are attained with this set-up. This clearly demonstrates that a certain ratio of amine to solvent may be used successfully, so long as the amine is still in excess of stoichiometric.

The following non-limiting examples will further illustrate the topics discussed above.

Raw materials were charged in a sequence described in the above general procedure. Table 1 describes various experiments with raw material charges, reaction temperature set point, % yield of isolated solids based on the amount of zinc used and assumes all of the zinc has reacted. In some experiments, some zinc had settled to the bottom of the reactor or had formed zinc lumps. In the yield calculation, the amount of unreacted zinc was not taken into account, but was calculated based on the amount of zinc charged. Also there was always some loss of solids in handling and this was not accounted for in the yield calculation. Methanol was used for dilution and for washing the product cake. The product was dried in an oven at 50 to 70° C. for several hours.

Zinc used from Fisher and from Aldrich (less than 10 microns) was 98+% assay whereas zinc from Johnson Matthey was 99.9% metal assay (−100 mesh). Bulab 600 is TMEDA obtained from Buckman Labs. TMEDA from Aldrich was 99% assay. Balab 600 has an assay greater than 98%.

EXAMPLES 1–3

These Experiments correspond to Nos. 1,5 and 6, respectively, in Table 1 and illustrate "normal" runs using fresh TMEDA and a molar ratio of TMEDA to zinc of about 6.6.

EXAMPLE 4

This Experiment corresponds to No. 2 in Table 1, where the molar ratio of TMEDA to zinc was kept at about 4.7 versus the normal runs. In this experiment after the reaction hold period at 90° C., the mixture was cooled to 30° C. and TMEDA was then decanted. After that 500 mL N-Methyl-2-pyrrolidone (NMP) was added and mixture was heated to 60° C. and filtered hot. To the filtrate was added 1000 mL methanol and mixture was cooled in an ice bath. The precipitated solids were filtered and washed with methanol and product was dried in an oven at 50 to 70° C. for several hours. This illustrates where product was recrystallized from NMP and methanol.

EXAMPLES 5 AND 6

These Examples correspond to Nos. 3 and 7, respectively, in Table 1. Decanted TMEDA obtained from other normal runs was used. It was discovered that the product yield was higher when decanted TMEDA was used.

EXAMPLES 7 AND 8

These Examples correspond to Nos. 4 and 8, respectively, in Table 1. Zinc from Johnson Matthey (99.9% pure and −100 mesh) was used. It was surprisingly discovered that the amount of TMEDA decanted in these runs was significantly higher compared to normal runs (Nos. 1,5 and 6).

EXAMPLES 9 AND 10

These Examples correspond to Nos. 9 and 10, respectively, in Table 1. Their purpose is to illustrate addition of a certain amount of solvent such as methanol to replace part of TMEDA used in the normal runs.

In No. 9 about 15% of TMEDA by weight was replaced with methanol and hence instead of TMEDA to zinc ratio being 6.6 it was 5.6. In this experiment, Zinc (40.8 g, 0.62 moles), Sulfur (120.2 g, 3.75 moles), TMEDA (408 g, 3.51 moles) and methanol (72 g) were charged to the reactor using the sequence described in general procedure. Although the set point for reaction temperature was kept at 90° C., the reaction temperature stabilized at 86° C. while under reflux. In this reaction, an exotherm was not observed and since the reaction was under reflux, the reaction temperature was steady at 86° C. After 6 hrs at 86° C., the mixture was cooled and liquid containing excess TMEDA and methanol was decanted. Then 500 mL methanol was added to the reaction mixture and the mixture was stirred for few minutes and vacuum filtered to give product which was washed with 200 mL methanol. The product was dried in an oven at 50 to 70° C. for several hours.

No. 10 was similar to No. 9 except that 50% by weight of TMEDA was replaced with methanol and hence instead of the TMEDA to zinc ratio being 6.6 it was 3.31. In this experiment, Zinc (20 g, 0.31 moles), Sulfur (60.7 g, 1.89 moles), TMEDA (117.5 g, 1.01 moles) and methanol (117.5 g) were charged to the reactor using the sequence described in general procedure. Although the set point for the reaction temperature was kept at 90° C., the reaction temperature stabilized at 72° C. while under reflux. In this reaction, an exotherm was not observed and since the reaction was under reflux, the reaction temperature did not exceed 72° C. After 7 hrs at 72° C., liquid containing excess TMEDA and methanol was decanted. Then 300 mL methanol was added to the reaction mixture and the mixture was stirred for few minutes and vacuum filtered to give product which was washed with 200 mL methanol. The product was dried in an oven at 50 to 70° C. for several hours.

EXAMPLES 11 AND 12

These Examples correspond to Experiment Nos. 11 and 12, respectively, in Table 1. Experiment Nos. 11 and 12 are solvent mediated reactions. In these reactions, the TMEDA to zinc ratio was kept at 1.5 (significantly lower). In experiment No. 11, the reaction mixture was kept at reflux temperature for several hours. In experiment No. 12, the reaction mixture was kept at 100–110° C. for several hours. There was no change in the reaction mixture during reaction and there was no sign of any color change indicative of reaction progress. The reaction mixture was filtered and solids obtained were dried. These solids were not the desired product and seemed mostly unreacted starting material or some other unknowns.

TABLE 1

| No. | Zinc Used gms | Moles of Zn | Sulfur used gms | Moles of S | Ratio S/Zn moles | TMEDA used gms | Moles of TMEDA | Ratio TMEDA to Zn moles | Rxn Time at 90° C. hrs |
|---|---|---|---|---|---|---|---|---|---|
| 1 | 65.4 | 1.00 | 195 | 6.08 | 6.08 | 770 | 6.63 | 6.62 | 3 |
| 2 | 32.7 | 0.50 | 96.2 | 3.00 | 6.00 | 275 | 2.37 | 4.73 | 2 |
| 3 | 98.1 | 1.50 | 297.3 | 9.27 | 6.18 | 1155 | 9.94 | 6.62 | 2.66 |
| 4 | 65.4 | 1.00 | 195 | 6.08 | 6.08 | 770 | 6.63 | 6.62 | 2.2 |

For the following batches Lightnin stirrer with A-310 blades dual/single was used.
For above batches glass rod with paddle was used.

| No. | Zinc Used gms | Moles of Zn | Sulfur used gms | Moles of S | Ratio S/Zn moles | TMEDA used gms | Moles of TMEDA | Ratio TMEDA to Zn moles | Rxn Time at 90° C. hrs |
|---|---|---|---|---|---|---|---|---|---|
| 5 | 81.8 | 1.25 | 250 | 7.80 | 6.23 | 962 | 8.28 | 6.62 | 2 |
| 6 | 81.8 | 1.25 | 250 | 7.80 | 6.23 | 962 | 8.28 | 6.62 | 2 |
| 7 | 81.8 | 1.25 | 250 | 7.80 | 6.23 | 962 | 8.28 | 6.62 | 2.25 |
| 8 | 65.4 | 1.00 | 198 | 6.17 | 6.17 | 770 | 6.63 | 6.62 | 3 |
| 9 | 40.8 | 0.62 | 120.2 | 3.75 | 6.01 | 408 | 3.51 | 5.63 | 6 |
| 10 | 20 | 0.31 | 60.7 | 1.89 | 6.19 | 117.5 | 1.01 | 3.31 | 7 hr/ 72° C. |
| 11 | 5 | 0.08 | 15.6 | 0.49 | 6.36 | 13.5 | 0.12 | 1.52 | Day |
| 12 | 5 | 0.08 | 15.6 | 0.49 | 6.36 | 13.5 | 0.12 | 1.52 | Day |

| No. | Product wt gms | % Yield | m.p ° C. | Total MeOH For dilution & washing | TMEDA Decanted gms | TMEDA Decanted % of charged | Zinc Used | TMEDA used |
|---|---|---|---|---|---|---|---|---|

TABLE 1-continued

| | | | | | | | | |
|---|---|---|---|---|---|---|---|---|
| 1 | 344 | 92 | 153–160 | 1500 | 217 | 28% | Fisher | Aldrich |
| 2 | 110.4 | 59.1 | 153–157 | 1000 | 72 | 26% | Fisher | Aldrich |
| 3 | 537 | 95.7 | 154–155 | 2000 | 426.5 | 37% | Aldrich | Decanted |
| 4 | 308 | 82.3 | 153–155 | 1500 | 413 | 54% | 99.90% | Aldrich |

For the following batches Lightnin stirrer with A-310 blades dual/single was used.
For above batches glass rod with paddle was used.

| | | | | | | | | |
|---|---|---|---|---|---|---|---|---|
| 5 | 419.5 | 89.7 | 153–158 | 1000 | 472 | 49% | Aldrich | Aldrich |
| 6 | 436.4 | 93.3 | 153–159 | 1000 | 474.1 | 49% | Aldrich | Bulab 600 |
| 7 | 444 | 94.9 | 158–160 | 1000 | 439.1 | 46% | Aldrich | Decanted |
| 8 | — | — | — | 700 | 528.4 | 69% | 99.9% Zn | Aldrich + Decanted |
| 9 | 199.8 | 85.6 | 153–158 | 700 | | | Aldrich | Bulab 600 |
| 10 | 104.5 | 91.3 | — | 450 | | | Aldrich | Aldrich |
| 11 | Heptane (150 mL) under reflux-did not work | | | | | | Aldrich | |
| 12 | Decane (100 mL) at 110° C.-did not work | | | | | | Aldrich | |

EXAMPLE 13

Use of ZHS

Use of 99.9% zinc in the process of the present invention not only demonstrated an advantage in separating the amine solvent from the product, but surprisingly, in the performance of the crude product in rubber. The performance in rubber compositions of complexed zinc hexasulfide product made from the higher purity zinc was compared to that of crude and recrystallized product made from lower purity zinc. The comparison was made using activating quantities (0.3 phr) of the zinc hexasulfide complex. The results of the comparison tests are shown in the following Tables 2, 3 and 4.

TABLE 2

OE TREAD COMPOUND 50:20:30 SBR/BR/NR

| Stock | 1 | 2 | 3 | 4 | 5 | 6 | 7 | 8 | 9 | 10 | 11 | 12 |
|---|---|---|---|---|---|---|---|---|---|---|---|---|
| Master | 166.0 | 166.0 | 166.0 | 166.0 | 166.0 | 166.0 | 166.0 | 166.0 | 166.0 | 166.0 | 166.0 | 166.0 |
| Crystex OT 10 | 1.5 | 1.5 | 1.5 | 1.5 | 1.5 | 1.5 | 1.5 | 1.5 | 1.5 | 1.5 | 1.5 | 1.5 |
| Santocure ® CBS | 1.0 | 1.0 | 1.0 | 1.0 | 1.0 | 1.0 | 1.0 | 1.0 | 1.0 | 1.0 | 1.0 | 1.0 |
| Santoflex ® 6PPD | 2.0 | 2.0 | 2.0 | 2.0 | 2.0 | 2.0 | 2.0 | 2.0 | 2.0 | 2.0 | 2.0 | 2.0 |
| Perkacit ® TMTD | — | 0.3 | — | — | — | — | — | — | — | — | — | — |
| Perkacit ® DPG | — | — | 0.3 | — | — | — | — | — | — | — | — | — |
| GBM 5601476 (AK8599) | — | — | — | 0.3 | — | — | — | — | — | — | — | — |
| PMM 2401-1 (AK8599) | — | — | — | — | 0.3 | — | — | — | — | — | — | — |
| PMM 2403-1 (AK8599) | — | — | — | — | — | 0.3 | — | — | — | — | — | — |
| PMM 2406-1 (AK8599) | — | — | — | — | — | — | 0.3 | — | — | — | — | — |
| PMM 2407-1 (AK8599) | — | — | — | — | — | — | — | 0.3 | — | — | — | — |
| PMM 2408-1 (AK8599) | — | — | — | — | — | — | — | — | 0.3 | — | — | — |
| PMM 2411-1 (AK8599) | — | — | — | — | — | — | — | — | — | 0.3 | — | — |
| PMM 2415-1 (AK8599) | — | — | — | — | — | — | — | — | — | — | 0.3 | — |
| JSL 5466682-1 (AK8599) | — | — | — | — | — | — | — | — | — | — | — | 0.3 |
| Mooney Scorch @ 121 C. | | | | | | | | | | | | |
| Min. Viscosity | 47.9 | 48.6 | 47.3 | 50.0 | 48.7 | 49.3 | 50.3 | 49.7 | 49.9 | 50.0 | 50.2 | 50.2 |
| t 5, Minutes | 45.5 | 27.6 | 33.0 | 26.4 | 30.3 | 28.2 | 25.6 | 28.8 | 29.1 | 26.4 | 26.4 | 31.3 |
| t 35, Minutes | 51.6 | 30.6 | 38.2 | 31.3 | 35.0 | 33.1 | 30.2 | 33.5 | 34.0 | 31.0 | 31.0 | 36.1 |
| t35–t2, Min. | 6.1 | 3.0 | 5.2 | 4.9 | 4.7 | 4.9 | 4.6 | 4.7 | 4.9 | 4.6 | 4.6 | 4.8 |
| Rheometer @ 150 C. | | | | | | | | | | | | |
| Max. Torque, dNm | 38.6 | 44.7 | 39.0 | 40.2 | 39.8 | 40.3 | 40.2 | 40.4 | 40.7 | 40.3 | 40.6 | 40.9 |
| Min. Torque, dMm | 7.1 | 7.1 | 7.0 | 7.4 | 7.2 | 7.3 | 7.4 | 7.3 | 7.4 | 7.4 | 7.5 | 7.6 |
| t 2, Minutes | 8.0 | 4.9 | 6.5 | 5.9 | 6.8 | 6.4 | 5.8 | 6.3 | 6.3 | 5.9 | 5.9 | 6.6 |
| t 25, Minutes | 10.2 | 5.8 | 8.0 | 7.5 | 8.5 | 8.1 | 7.4 | 8.0 | 8.0 | 7.5 | 7.5 | 8.3 |
| t 50, Minutes | 11.6 | 6.4 | 8.8 | 8.5 | 9.6 | 9.1 | 8.4 | 9.1 | 9.0 | 8.5 | 8.5 | 9.4 |
| t 90, Minutes | 16.6 | 8.5 | 12.5 | 12.5 | 13.9 | 13.3 | 12.3 | 13.2 | 13.3 | 12.5 | 12.5 | 13.8 |
| t25–t2, Minutes | 2.2 | 0.9 | 1.5 | 1.6 | 1.7 | 1.7 | 1.6 | 1.7 | 1.7 | 1.6 | 1.6 | 1.7 |
| t50–t2, Minutes | 3.6 | 1.5 | 2.3 | 2.6 | 2.8 | 2.7 | 2.6 | 2.8 | 2.7 | 2.6 | 2.6 | 2.8 |
| t90–t2, Minutes | 8.6 | 3.6 | 6.0 | 6.6 | 7.1 | 6.9 | 6.5 | 6.9 | 7.0 | 6.6 | 6.6 | 7.2 |
| % Reversion | 0.0 | 1.5 | 0.0 | 0.0 | 0.0 | 0.0 | 0.0 | 0.0 | 0.0 | 0.0 | 0.0 | 0.0 |
| Rheometer @ 160 C. | | | | | | | | | | | | |
| Max. Torque, dNm | 37.8 | 43.7 | 38.6 | 39.6 | 39.6 | 40.0 | 39.6 | 39.8 | 40.0 | 39.7 | 39.8 | 40.1 |
| Min. Torque, dNm | 6.8 | 6.7 | 6.7 | 7.0 | 7.0 | 7.0 | 7.1 | 7.1 | 7.1 | 7.1 | 7.2 | 7.2 |
| t 90, Minutes | 10.2 | 4.9 | 7.4 | 7.7 | 8.3 | 8.1 | 7.7 | 8.0 | 8.0 | 7.7 | 7.7 | 8.3 |
| t 2, Minutes | 4.8 | 2.9 | 3.8 | 3.6 | 3.9 | 3.8 | 3.5 | 3.7 | 3.7 | 3.5 | 3.5 | 3.8 |
| t 90–t 2, Minutes | 5.4 | 2.0 | 3.6 | 4.1 | 4.4 | 4.3 | 4.2 | 4.3 | 4.3 | 4.2 | 4.2 | 4.5 |
| % Reversion | 4.0 | 6.6 | 5.2 | 5.3 | 5.1 | 5.6 | 4.9 | 5.0 | 5.1 | 5.1 | 5.1 | 4.8 |

TABLE 3

OE TREAD COMPOUND 50:20:30 SBR/BR/NR (245-010)

| Stock | 1 | 2 | 3 | 4 | 5 | 6 | 7 | 8 | 9 | 10 | 11 | 12 |
|---|---|---|---|---|---|---|---|---|---|---|---|---|
| Master | 166.0 | 166.0 | 166.0 | 166.0 | 166.0 | 166.0 | 166.0 | 166.0 | 166.0 | 166.0 | 166.0 | 166 |
| Crystex OT 10 | 1.5 | 1.5 | 1.5 | 1.5 | 1.5 | 1.5 | 1.5 | 1.5 | 1.5 | 1.5 | 1.5 | 1.5 |
| Santocure ® CBS | 1.0 | 1.0 | 1.0 | 1.0 | 1.0 | 1.0 | 1.0 | 1.0 | 1.0 | 1.0 | 1.0 | 1.0 |
| Santoflex ® 6PPD | 2.0 | 2.0 | 2.0 | 2.0 | 2.0 | 2.0 | 2.0 | 2.0 | 2.0 | 2.0 | 2.0 | 2.0 |
| Perkacit ® TMTD | — | 0.3 | — | — | — | — | — | — | — | — | — | — |
| Perkacit ® DPG | — | — | 0.3 | — | — | — | — | — | — | — | — | — |
| GBM 5601476 (AK8599) | — | — | — | 0.3 | — | — | — | — | — | — | — | — |
| PMM 2401-1 (AK8599) | — | — | — | — | 0.3 | — | — | — | — | — | — | — |
| PMM 2403-1 (AK8599) | — | — | — | — | — | 0.3 | — | — | — | — | — | — |
| PMM 2406-1 (AK8599) | — | — | — | — | — | — | 0.3 | — | — | — | — | — |
| PMM 2407-1 (AK8599) | — | — | — | — | — | — | — | 0.3 | — | — | — | — |
| PMM 2408-1 (AK8599) | — | — | — | — | — | — | — | — | 0.3 | — | — | — |
| PMM 2411-1 (AK8599) | — | — | — | — | — | — | — | — | — | 0.3 | — | — |
| PMM 2415-1 (AK8599) | — | — | — | — | — | — | — | — | — | — | 0.3 | — |
| JSL 5466682-1 (AK8599) | — | — | — | — | — | — | — | — | — | — | — | 0.3 |
| Stress-Strain Data (Unaged) Cured (t90 Min.) @ 150 C. | | | | | | | | | | | | |
| Tensile, Mpa | 23.5 | 15.5 | 25.4 | 24.0 | 19.8 | 22.5 | 22.7 | 18.8 | 21.6 | 24.2 | 22.8 | 22.4 |
| 100% Modulus, Mpa | 2.0 | 2.9 | 2.1 | 2.2 | 2.1 | 2.1 | 2.1 | 2.1 | 2.2 | 2.0 | 2.2 | 2.2 |
| 300% Modulus, Mpa | 9.4 | 13.8 | 10.4 | 10.4 | 10.3 | 9.9 | 10.5 | 10.4 | 10.5 | 10.0 | 11.1 | 11.0 |
| % Elongation | 580 | 328 | 587 | 551 | 478 | 536 | 533 | 453 | 507 | 552 | 513 | 515 |
| Shore "A" Hardness | 60 | 65 | 62 | 61 | 60 | 61 | 61 | 61 | 61 | 61 | 61 | 62 |
| Stress-Strain Data (Aged) Hot Air Aged 14 Days @ 70 C. | | | | | | | | | | | | |
| Tensile, Mpa | 21.8 | 14.5 | 23.3 | 23.8 | 17.8 | 20.0 | 19.1 | 17.2 | 19.6 | 21.6 | 19.2 | 16.3 |
| 100% Modulus, Mpa | 3.0 | 4.4 | 3.1 | 3.2 | 3.3 | 3.2 | 3.2 | 3.1 | 3.1 | 3.4 | 3.3 | 3.2 |
| 300% Modulus, Mpa | 13.8 | 0.0 | 14.1 | 14.8 | 15.0 | 14.6 | 14.9 | 14.5 | 14.3 | 15.4 | 15.2 | 14.8 |
| % Elongation | 440 | 236 | 465 | 461 | 352 | 387 | 378 | 346 | 389 | 414 | 354 | 328 |
| Shore "A" Hardness | 66 | 70 | 65 | 67 | 67 | 67 | 65 | 66 | 67 | 67 | 66 | 67 |

TABLE 4

OE TREAD COMPOUND 50:20:30 SBR/BR/NR (245-010)

| Stock | 1 | 2 | 3 | 4 | 5 | 6 | 7 | 8 | 9 | 10 | 11 | 12 |
|---|---|---|---|---|---|---|---|---|---|---|---|---|
| Master | 166.0 | 166.0 | 166.0 | 166.0 | 166.0 | 166.0 | 166.0 | 166.0 | 166.0 | 166.0 | 166.0 | 166.0 |
| Crystex OT 10 | 1.5 | 1.5 | 1.5 | 1.5 | 1.5 | 1.5 | 1.5 | 1.5 | 1.5 | 1.5 | 1.5 | 1.5 |
| Santocure ® CBS | 1.0 | 1.0 | 1.0 | 1.0 | 1.0 | 1.0 | 1.0 | 1.0 | 1.0 | 1.0 | 1.0 | 1.0 |
| Santoflex ® 6PPD | 2.0 | 2.0 | 2.0 | 2.0 | 2.0 | 2.0 | 2.0 | 2.0 | 2.0 | 2.0 | 2.0 | 2.0 |
| Perkacit ® TMTD | — | 0.3 | — | — | — | — | — | — | — | — | — | — |
| Perkacit ® DPG | — | — | 0.3 | — | — | — | — | — | — | — | — | — |
| GBM 5601476 (AK8599) | — | — | — | 0.3 | — | — | — | — | — | — | — | — |
| PMM 2401-1 (AK8599) | — | — | — | — | 0.3 | — | — | — | — | — | — | — |
| PMM 2403-1 (AK8599) | — | — | — | — | — | 0.3 | — | — | — | — | — | — |
| PMM 2406-1 (AK8599) | — | — | — | — | — | — | 0.3 | — | — | — | — | — |
| PMM 2407-1 (AK8599) | — | — | — | — | — | — | — | 0.3 | — | — | — | — |
| PMM 2408-1 (AK8599) | — | — | — | — | — | — | — | — | 0.3 | — | — | — |
| PMM 2411-1 (AK8599) | — | — | — | — | — | — | — | — | — | 0.3 | — | — |
| PMM 2415-1 (AK8599) | — | — | — | — | — | — | — | — | — | — | 0.3 | — |
| JSL 5466682-1 (AK8599) | — | — | — | — | — | — | — | — | — | — | — | 0.3 |
| Die C Tear (ASTM D624-91) 24 C. | | | | | | | | | | | | |
| Peak Stress, N/mm | 40.6 | 33.1 | 38.7 | 40.2 | 40.8 | 42.4 | 39.3 | 42.4 | 51.5 | 44.7 | 41.9 | 37.2 |
| Die C Tear (ASTM D624-91) 100 C. | | | | | | | | | | | | |
| Peak Stress, N/mm | 37.7 | 0.0 | 37.7 | 38.9 | 33.9 | 38.6 | 37.1 | 36.7 | 39.4 | 40.9 | 39.0 | 35.4 |
| DeMattia D813-87 (Unaged/Cut) | | | | | | | | | | | | |
| Kilocycles to Failure | 1000 | 20 | 1000 | 1000 | 1000 | 1000 | 1000 | 1000 | 1000 | 1000 | 1000 | 1000 |
| Goodrich Flex (225 psi/.225'/100 C.) Cured 3 × t90 Min. @ 160 C. | | | | | | | | | | | | |

TABLE 4-continued

OE TREAD COMPOUND 50:20:30 SBR/BR/NR (245-010)

| Stock | 1 | 2 | 3 | 4 | 5 | 6 | 7 | 8 | 9 | 10 | 11 | 12 |
|---|---|---|---|---|---|---|---|---|---|---|---|---|
| Delta T | 55.0 | 29.0 | 59.0 | 56.0 | 53.0 | 51.5 | 49.5 | 50.5 | 50.5 | 49.0 | 51.5 | 51.0 |
| % Permanent Set (30 Min.) | 28.1 | 9.5 | 33.4 | 28.0 | 29.6 | 28.1 | 26.9 | 26.2 | 27.6 | 27.3 | 28.8 | 26.9 |
| Blow Time in Minutes | 30 | 30 | 30 | 30 | 30 | 30 | 30 | 30 | 30 | 30 | 30 | 30 |

With regard to terms used above, the following applies:
1. Crystex® OT 10 is insoluble sulfur comprising about 90% total sulfur and about 10% additive oil.
2. Santocure®CBS is N-Cyclohexyl-2-benzothiazolesulfenamide.
3. Santoflex® 6PPD is N-(1,3-Dimethylbutyl)-N'-phenyl-p-phenylenediamine.
4. Perkacit® TMTD is Tetramethylthiuram disulfide.
5. Perkacit® DPG is N,N'-Diphenylguanidine.
6. GBM 5601476(AK8599), PMM2415-1, PMM 2406-1 and PMM 2411-1 are zinc hexasulfide amine complexes (ZHS) that have not been recrystallized, but based on 98+% purity zinc.
7. PMM 2401-1, PMM 2403-1 and JSL 5466682-1 are ZHS that have been recrystallized.
8. PMM 2407-1 and PPM 2408-1 are derived from 99.99% purity zinc.
9. Solflex 1216 is styrene butadiene rubber.
10. BR 1203 is butadiene rubber.
11. SMR CV60 is natural rubber.
12. N-339 is carbon black.
13. Sundex 8125 is extender oil.
14. "Master" has the following composition:

|  | Phr |
|---|---|
| Solflex 1216 | 50 |
| BR 1203 | 20 |
| SMR CV60 | 30 |
| N-339 Black | 50 |
| Sundex 8125 | 8 |
| Zinc Oxide | 5 |
| Stearic Acid | 3 |
| Banbury Master | 166 |

It can be observed from the above Tables 2, 3 and 4 that Productivity (t90) for all ZHS containing stocks was improved over the control stock(1) by approximately 3 minutes at 150° C. cure temperature. Other control stocks with commonly used activators, TMTD (tetramethylthiuram disulfide) (2) and DPG (N,N'-diphenylguanidine) (3), suggest that the zinc hexasulfide complexes activate (compare t90) rubber vulcanization in a manner comparable to that of DPG rather than TMTD.

Processing safety as measured by Mooney scorch time is an important criterion for the manufacture of rubber products. In numerous instances, impure sulfur and amine derived rubber additives have resulted in decreased processing safety of the rubber compound. The processing safety of rubber stocks 8&9, containing crude ZHS made from 99.9% zinc, compare favorably with that observed for stocks 5&6 which contain recrystallized ZHS (compare t5). Clearly, the Mooney scorch time exhibited in stocks 8&9 falls into the range for the recrystallized samples (see stocks 5&6).

Thus, the crude product derived from high purity zinc performs like recrystallized product in rubber, but has an advantage of reducing the number of manufacturing steps required to make ZHS(e.g. manufacture of acceptable ZHS without a purification step). This unexpected result has the direct affect of decreasing the manufacturing cost of the product without adversely affecting performance in rubber.

The physical properties presented in the tables show that the aging, tear, and flex characteristics are essentially no different for stocks 8&9 (99.9% zinc derived crude product) vs. 5&6 (recrystallized product). However, modest improvements in compression set and heat build-up are observed for 99.9% zinc derived product contained in stocks 8&9.

We claim:
1. A process for the manufacture of zinc hexasulfide amine complexes comprising reacting zinc, sulfur and a molar excess of amine at an elevated temperature to obtain a reaction mixture comprising zinc hexasulfide amine complexes and excess amine, adding a first solvent to the reactants or to the reaction mixture in which the zinc hexasulfide amine complexes are largely not soluble in an amount sufficient to obtain a slurry of said reaction mixture in said first solvent suitable for a subsequent separation process in which zinc hexasulfide amine complexes are to be recovered, most of the excess amine being separated from solid zinc hexasulfide amine complexes in the reaction mixture prior to addition of said first solvent by a technique such as decantation, filtering and/or siphoning and recovering zinc hexasulfide amine complexes product as a solid in said subsequent process.

2. The process of claim 1 wherein most of the excess amine is separated from solid zinc hexasulfide amine complexes in the reaction mixture by filtering and said product is washed with said first solvent to remove excess amine and impurities.

3. The process of claim 1 wherein said amine is not miscible with said first solvent.

4. The process of claim 2 wherein the reaction mixture is filtered and the product is washed with said first solvent and the filtrate forms two liquid phases comprising a first solvent phase and an amine phase, first solvent and amine being recycled and reused in the process.

5. The process of claim 1 wherein zinc hexasulfide amine complexes are separated from said reaction mixture as a cake of solids, said cake being washed to minimize color and/or odor from zinc hexasulfide amine complexes product.

6. The process of claim 5 wherein said cake is washed with an aqueous solution of a caustic and/or hypochlorite.

7. A process for the manufacture of zinc hexasulfide amine complexes comprising reacting zinc, which is at least about 99.5% pure with a particle size of −100 mesh, with sulfur and a molar excess of amine at an elevated temperature to obtain a reaction mixture comprising zinc hexasulfide amine complexes and excess amine, separating most of the excess amine from solid zinc hexasulfide amine complexes in the reaction mixture by a technique such as decanting, filtering and/or siphoning, adding a solvent to the reaction mixture in which the zinc hexasulfide amine complexes are not soluble and recovering zinc hexasulfide amine complexes product by filtering zinc hexasulfide amine complexes as solids from the reaction mixture and drying said solids to obtain said product.

8. The process of claim 7 wherein said amine and said solvent are immiscible, the filtrate recovered from the filtering of zinc hexasulfide amine complexes being two liquid phases comprising a solvent phase and an amine phase, each of which are recycled and reused in the process.

* * * * *